United States Patent [19]

Sirrenberg et al.

[11] Patent Number: 5,096,928
[45] Date of Patent: Mar. 17, 1992

[54] INSECTICIDAL SUBSTITUTED BENZOYL(THIO) UREAS

[75] Inventors: Wilhelm Sirrenberg, Sprockhoevel; Albrecht Marhold, Leverkusen; Benedikt Becker, Mettmann; Wilhelm Stendel, Wuppertal, all of Fed. Rep. of Germany

[73] Assignee: Bayer Aktiengesellschaft, Leverkusen, Fed. Rep. of Germany

[21] Appl. No.: 587,596

[22] Filed: Sep. 24, 1990

Related U.S. Application Data

[63] Continuation of Ser. No. 276,720, Nov. 28, 1988, abandoned.

[30] Foreign Application Priority Data

Dec. 2, 1987 [DE] Fed. Rep. of Germany ....... 3740807

[51] Int. Cl.$^5$ ................. C07C 275/54; C07C 335/26; A01N 47/34
[52] U.S. Cl. .................................. 514/584; 514/594; 558/17; 564/23; 564/44
[58] Field of Search .............. 564/23, 44; 558/17; 514/584, 594

[56] References Cited

U.S. PATENT DOCUMENTS

| | | | |
|---|---|---|---|
| 4,734,436 | 3/1988 | Kurozumi et al. | 564/44 |
| 4,782,090 | 11/1988 | Sirrenberg et al. | 564/44 |
| 4,782,091 | 11/1988 | Sirrenberg et al. | 564/44 |

FOREIGN PATENT DOCUMENTS

| | | |
|---|---|---|
| 0246061 | 11/1987 | European Pat. Off. |
| 0268943 | 6/1988 | European Pat. Off. |
| 0268952 | 6/1988 | European Pat. Off. |

*Primary Examiner*—Richard L. Raymond
*Attorney, Agent, or Firm*—Sprung Horn Kramer & Woods

[57] ABSTRACT

Insecticidal substituted benzoyl(thio) ureas of the formula

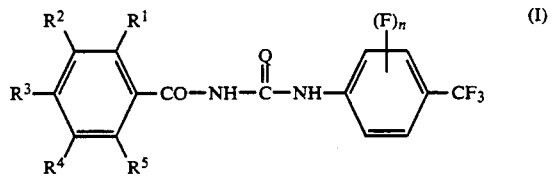

in which
Q stands for oxygen or sulphur,
$R^1$ stands for hydrogen, halogen, nitro, methyl or trifluoromethyl,
$R^2$ stands for hydrogen, fluorine or chlorine,
$R^3$ stands for hydrogen, fluorine or chlorine,
$R^4$ stands for hydrogen or fluorine,
$R^5$ stands for hydrogen or halogen and
n stands for the numbers 2, 3 or 4.

Intermediates of the formula

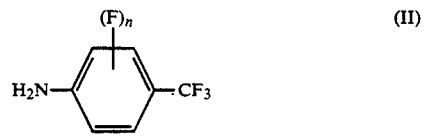

and

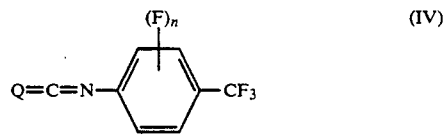

are also new.

17 Claims, No Drawings

INSECTICIDAL SUBSTITUTED BENZOYL(THIO) UREAS

This application is a continuation of application Ser. No. 276,720, filed 11/28/88, now abandoned.

The present invention relates to new substituted benzoyl(thio)ureas, processes and new intermediates for the preparation thereof, and to their use as pesticides, in particular as insecticides.

It is already known that certain benzoylureas, such as, for example, 1-(2-chloro-benzoyl)-3-(4-chloro-3-trifluoromethyl-phenyl)-urea, 1-(2,6-difluoro-benzoyl)-3-4(4-fluoro-3-trifluoromethyl-phenyl)-urea, 1-(2,6-dichloro-benzoyl)-3-(4-fluoro-3-trifluoromethyl-phenyl)-urea, 1-(2,6-difluorobenzoyl)-3-(4-trifluoromethyl-phenyl)-urea and 1-(2,6-difluoro-benzoyl)-3-(3,5-dichloro-2,4-difluorophenyl)-urea, exhibit insecticidal properties (cf. U.S. Pat. No. 4,085,226 issued Apr. 18, 1988, DE-OS (German Published Specification) 2,123,236 and EP-A 52,833).

The new substituted benzoyl(thio)ureas of the general formula (I)

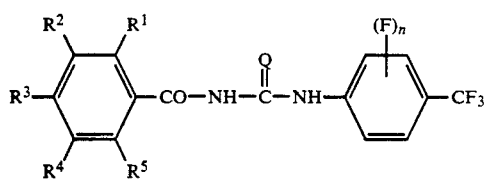

in which
Q stands for oxygen or sulphur,
R¹ stands for hydrogen, halogen, nitro, methyl or trifluoromethyl,
R² stands for hydrogen, fluorine or chlorine,
R³ stands for hydrogen, fluorine or chlorine,
R⁴ stands for hydrogen or fluorine,
R⁵ stands for hydrogen or halogen and
n stands for the numbers 2, 3 or 4, have now been found.

Furthermore, it has been found that the new substituted benzoyl(thio)ureas of the general formula (I) are obtained when (a) substituted anilines of the general formula (II)

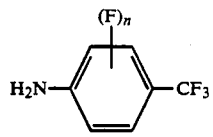

in which
n has the abovementioned meaning,
are reacted with benzoyl iso(thio)cyanates of the general formula (III)

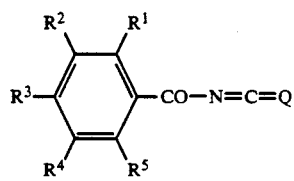

in which

Q, R¹, R², R³, R⁴ and R⁵ have the abovementioned meanings,
if appropriate in the presence of a diluent, or (b) substituted phenyl iso(thio)cyanates of the general formula (IV)

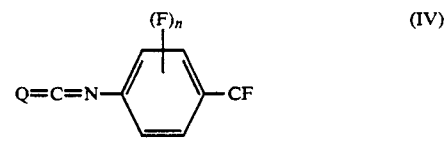

in which
Q and n have the abovementioned meanings,
are reacted with benzamides of the general formula (V)

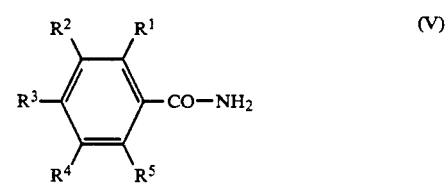

in which
R¹, R², R³, R⁴ and R⁵ have the abovementioned meanings,
if appropriate in the presence of a catalyst and if approprite in the presence of a diluent.

The new compounds of the general formula (I) possess surprising, advantageous properties which enable them to be used as pesticides; they show good arthropodicidal properties and are distinguished in particular by a very strong insecticidal activity.

In the general formulae, halogen denotes fluorine, chlorine, bromine and iodine, preferably fluorine, chlorine and bromine, particularly preferably fluorine or chlorine.

n preferably stands for 2 or 3, the fluorine atoms being preferably in the 3,5- and 3,5,6-positions.

Preferred new substituted benzoyl(thio)ureas of the formula (I) are those in which
Q stands for oxygen or sulphur,
R¹ stands for hydrogen, fluorine, chlorine, nitro, methyl or trifluoromethyl (preferably for fluorine, chlorine or methyl),
R² stands for hydrogen, fluorine or chlorine,
R³ stands for hydrogen, fluorine or chlorine,
R⁴ stands for hydrogen or fluorine,
R⁵ stands for hydrogen, fluorine or chlorine and
n stands for the numbers 2, 3 or 4.

Particularly preferred new substituted benzoyl(thio)ureas of the formula (I) are those in which
Q stands for oxygen or sulphur (preferably oxygen),
R¹ stands for fluorine or chlorine,
R² stands for hydrogen,
R³ stands for hydrogen or fluorine,
R⁴ stands for hydrogen or fluorine (preferably hydrogen),
R⁵ stands for hydrogen or fluorine and
n stands for the numbers 2, 3 or 4 (preferably 2 or 3).

Examples of compounds of the formula (I) are listed in the following Table 1 [and also in the Preparation Examples hereinbelow.

TABLE 1
Examples of the compounds of the formula (I)
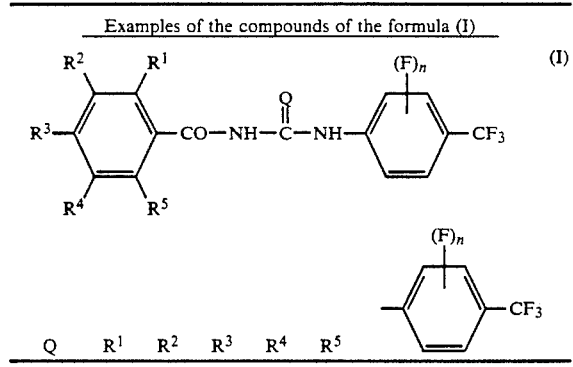
| Q | R¹ | R² | R³ | R⁴ | R⁵ | (F)ₙ / CF₃ group |
|---|----|----|----|----|----|------------------|
| O | F  | H  | H  | H  | F  | 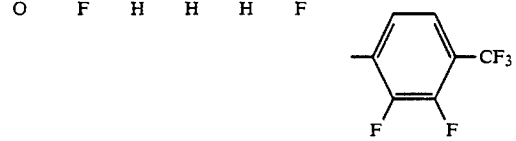 |
| S | F  | H  | H  | H  | F  | 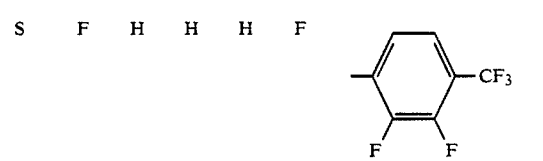 |
| O | Cl | H  | H  | H  | H  | 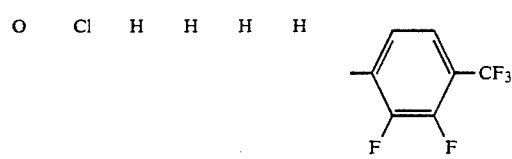 |
| S | Cl | H  | H  | H  | H  | 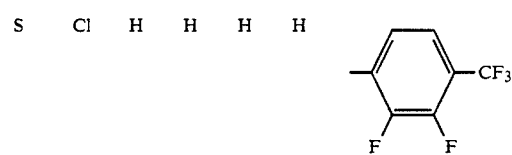 |
| O | Cl | H  | H  | H  | F  | 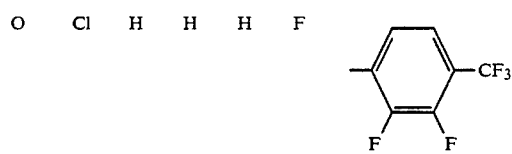 |
| S | Cl | H  | H  | H  | F  | 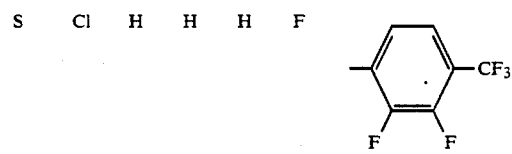 |
| O | Cl | H  | F  | H  | H  | 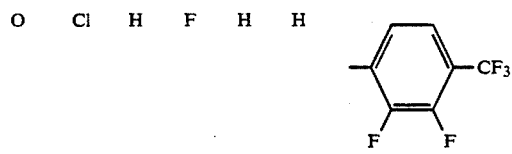 |
| S | Cl | H  | F  | H  | H  | 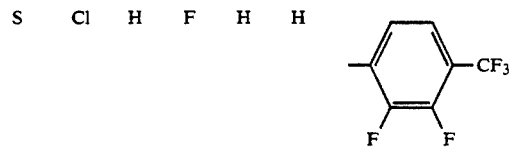 |
TABLE 1-continued
Examples of the compounds of the formula (I)
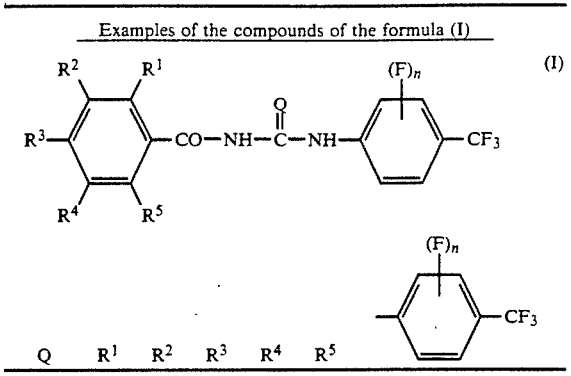
| Q | R¹ | R² | R³ | R⁴ | R⁵ | (F)ₙ / CF₃ group |
|---|----|----|----|----|----|------------------|
| O | Cl | H  | H  | F  | H  | 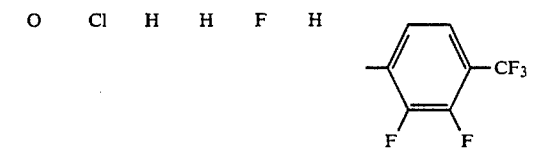 |
| S | Cl | H  | H  | F  | H  | 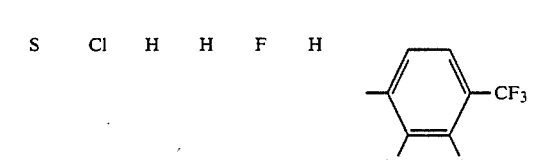 |
| O | F  | H  | H  | H  | H  | 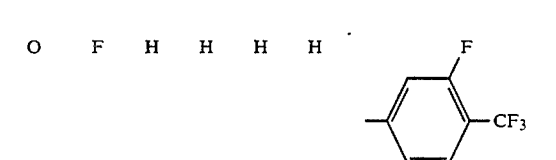 |
| S | F  | H  | H  | H  | H  | 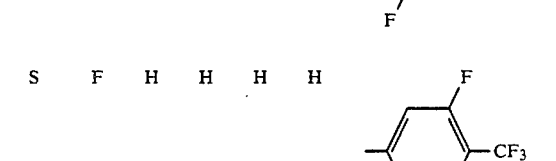 |
| O | Br | H  | H  | H  | H  | 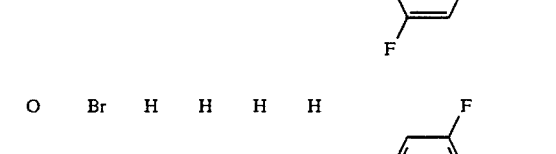 |
| S | Br | H  | H  | H  | H  | 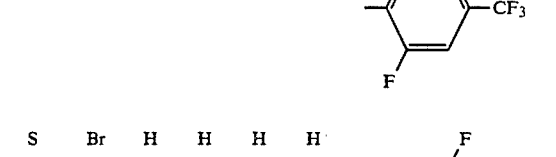 |
| O | Cl | H  | H  | H  | H  |  |

TABLE 1-continued

Examples of the compounds of the formula (I)

(I)

R²—R¹
R³—⟨benzene⟩—CO—NH—C(=Q)—NH—⟨benzene (F)n⟩—CF₃
R⁴—R⁵

| Q | R¹ | R² | R³ | R⁴ | R⁵ | ⟨(F)n-phenyl⟩-CF₃ |
|---|----|----|----|----|----|--------------------|
| S | Cl | H | H | H | H | 2,5-F₂-phenyl-CF₃ |
| O | F | H | H | H | F | 2,5-F₂-phenyl-CF₃ |
| O | Cl | H | H | H | F | 2,5-F₂-phenyl-CF₃ |

If, for example, 2,5-difluoro-4-trifluoromethylaniline and 2-fluorobenzoyl isothiocyanate are used as starting substances in process variant (a), the course of the reaction can be represented by the following equation:

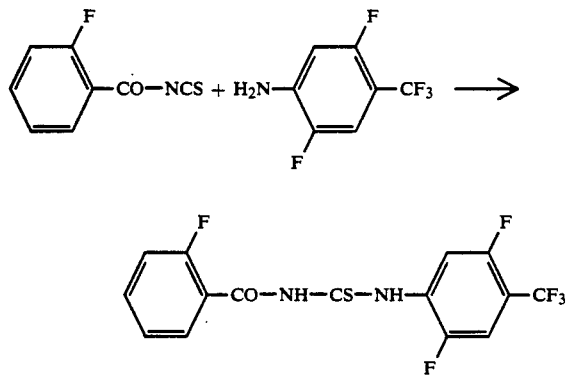

If, for example, 2,3-difluoro-4-trifluoromethylphenyl isocyanate and 2,4-difluoro-benzamide are used as starting substances in process variant (b), the course of the reaction can be represented by the following equation:

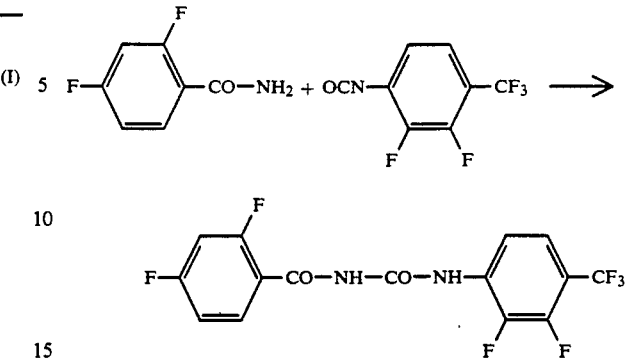

Formula (II) provides a general definition of the substituted anilines to be used as starting substances in process (a) according to the invention. In formula (II), n preferably, or in particular, has the meaning which has already been indicated as preferred in connection with the description of the compounds of the formula (I) according to the invention as being preferred, or particularly preferred, respectively.

The following may be mentioned as examples of the starting substances of the formula (II): 2,3-difluoro-4-trifluoromethyl-aniline, 2,5-difluoro-4-trifluoromethylaniline, 2,6-difluoro-4-trifluoromethyl-aniline, 3,5-difluoro-4-trifluoromethyl-aniline, 2,3,5-trifluoro-4-trifluoromethyl-aniline, 2,3,6-trifluoro-4-trifluoromethylaniline and 2,3,5,6-tetrafluoro-4-trifluoromethyl-aniline.

The starting substances of the formula (II) are new.

The compounds of the formula (II) are obtained when benzotrifluoride derivatives of the general formula (VI)

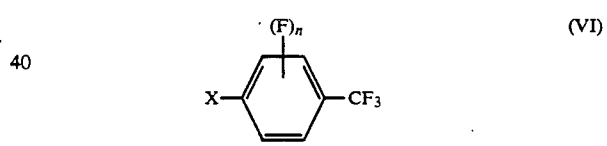

in which
n has the abovementioned meaning and
X stands for fluorine or chlorine are reacted with ammonia at an increased pressure up to about 20 bar and at temperatures between 10° C. and 150° C., if appropriate in the presence of a diluent, such as, for example, tetrahydrofuran or dioxane, and the product of the formula (II) is isolated by distillation under reduced pressure.

Formula (III) provides a general definition of the benzoyl iso(thio)cyanates also to be employed as starting substances in process (a). In formula (III), Q, R¹, R², R³, R⁴ and R⁵ preferably, or in particular, have those meanings which have already been indicated in connection with the description of the compounds of the formula (I) according to the invention as being preferred, or particularly preferred, respectively, for Q, R¹, R², R³, R⁴ and R⁵.

The following may be mentioned as examples of the starting substances of the formula (III): 2-fluoro-, 2-chloro-, 2-bromo-, 2-iodo-, 2,6-difluoro-, 2,4-difluoro-, 2-chloro-4-fluoro-, 2-chloro-6-fluoro-, 2-chloro-5-fluoro-, 2,3,6-trichloro-, 2,3,4,5,6-pentafluoro-, 2,4-dichloro-5-fluoro-, 2-methyl-, 2-nitro-, 2-trifluoromethyl-, 2,6-dichloro-, 2,4-dichloro- and 4-chloro-benzoyl isocyanate or -benzoyl isothiocyanate.

The starting substances of the formula (III) are known and/or can be prepared by processes known per se (cf. DE-OS (German Published Specification) 2,123,236, DE-OS (German Published Specification) 2,504,982, DE-OS (German Published Specification) 2,601,780, DE-OS (German Published Specification) 2,801,316, DE-OS (German Published Specification) 2,837,086, DE-OS (German Published Specification) 3,217,619 and DE-OS (German Published Specification) 3,217,620).

Formula (IV) provides a general definition of the substituted phenyl iso(thio)cyanates to be used as starting substances in process (b) according to the invention. In formula (IV), Q and n preferably, or in particular, have those meanings which have already been indicated in connection with the description of the compounds of the formula (I) according to the invention as being preferred, or particularly preferred, respectively.

The following may be mentioned as examples of the starting substances of the formula (IV): 2,3-difluoro-4-trifluoromethyl-, 2,5-difluoro-4-trifluoromethyl-, 2,6-difluoro-4-trifluoromethyl-, 3,5-difluoro-4-trifluoromethyl-, 2,3,5-trifluoro-4-trifluoromethyl-, 2,3,6-trifluoro-4-tri- fluoromethyl- and 2,3,5,6-tetrafluoro-4-trifluoromethylphenyl isocyanate or -phenyl isothiocyanate, respectively.

The starting substances of the formula (IV) are new and are part of the present invention.

The compounds of the formula (IV) are obtained when corresponding substituted anilines of the general formula (II) are reacted in a customary manner with phosgene or thiophosgene, if appropriate in the presence of a diluent, such as, for example, toluene, chlorobenzene, xylene or o-dichlorobenzene, at temperatures between 0° C. and 150° C., and the reaction product is then distilled under reduced pressure.

Formula (V) provides a general definition of the benzamides to be also used as starting substances in process (b). In formula (V), $R^1$, $R^2$, $R^3$, $R^4$ and $R^5$ preferably, or in particular, have those meanings which have already been indicated in connection with the description of the compounds of the formula (I) according to the invention as being preferred, or particularly preferred, respectively.

The following may be mentioned as examples of the starting substances of the formula (V): 2-fluoro-, 2-chloro-, 2-bromo-, 2-iodo-, 2,6-difluoro-, 2,4-difluoro-, 2-chloro-6-fluoro-, 2-chloro-4-fluoro-, 2-chloro-5-fluoro-, 2,3,6-trichloro-, 2,3,4,5,6-pentafluoro-, 2,4-dichloro-5-fluoro-, 2-methyl-, 2-nitro-, 2-trifluoromethyl-, 2,6-di- chloro-, 2,4-dichloro- and 4-chloro-benzamide.

The starting substances of the formula (V) are known and/or can be prepared by processes known per se (cf. literature for the starting substances of the formula (III)).

Suitable diluents for carrying out process variants (a) and (b) are virtually all inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chlorine, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone and methyl ethyl, methyl isopropyl and methyl isobutyl ketone, esters, such as methyl and ethyl acetate, nitriles, such as, for example, acetonitrile and propionitrile, amides, such as, for example, dimethylformamide, dimethylacetamide and N-methylpyrrolidone, and tetramethylene sulphone.

Catalysts which can be used for the reaction in accordance with process variant (b) preferably include tertiary amines, such as triethylamine and 1,4-diazobicyclo[2,2,2]-octane, and organotin compounds, such as, for example, dibutyltin dilaurate. However, the addition of such catalysts is not absolutely necessary.

In process variants (a) and (b), the reaction temperature can be varied within a relatively wide range. In general, process variant (a) is carried out between 20° C. and 180° C., preferably between 40° C. and 120° C., and process variant (b) is carried out between 20° C. and 200° C., preferably between 60° C. and 190° C. The process variants according to the invention are generally carried out under atmospheric pressure.

For carrying out the process variants according to the invention, the starting substances are usually employed in approximately equimolar amounts. An excess of one or the other of the reaction components does not constitute any considerable advantages.

Working up of the reaction products is carried out by customary methods, for example by filtering off the precipitated product by suction, or by removing undesired by-products from the reaction mixture by dissolution. The melting point is used for characterization.

The compounds of the general formula (I) are suitable for combating animal pests, preferably arthropods, in particular insects, which are encountered in agriculture, in forestry, in the protection of stored products and of materials, and in the hygiene field. They are active against normally sensitive and resistant species and against all or some stages of development. The abovementioned pests include:

From the order of the Isopoda, for example, Oniscus asellus, Armadillidium vulgare and Porcellio scaber. From the order of the Diplopoda, for example, Blaniulus guttulatus. From the order of the Chilopoda, for example, Geophilus carpophagus and Scutigera spec. From the order of the Symphyla, for example, Scutigerella immaculata. From the order of the Thysanura, for example, Lepisma saccharina. From the order of the Collembola, for example, Onychiurus armatus. From the order of the Orthoptera, for example, Blatta orientalis, Periplaneta americana, Leucophaea maderae, Blattella germanica, Acheta domesticus, Gryllotalpa spp., Locusta migratoria migratorioides, Melanoplus differentialis and Schistocerca gregaria. From the order of the Dermaptera, for example, Forficula auricularia. From the order of the Isoptera, for example, Reticulitermes spp. From the order of the Anoplura, for example, Phylloxera vastatrix, Pemphigus spp., Pediculus humanus corporis, Haematopinus spp. and Linognathus spp. From the order of the Mallophaga, for example, Trichodectes spp. and Damalinea spp. From the order of the Thysanoptera, for example, Hercinothrips fermoralis and Thrips tabaci. From the order of the Heteroptera, for example, Eurygaster spp., Dysdercus intermedius, Piesma quadrata, Cimex lectularius, Rhodnius prolixus and Triatoma spp. From the order of the Homoptera, for example, Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp. From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana. From the order of the Coleoptera, for example, Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varive stis, Atomaria spp., Oryzaephilus surinamensis, Antho nomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Cono derus spp., Melolontha melolontha, Amphimallon solsti tialis and Costelytra zealandica. From the order of the Hymenoptera, for example, Diprion spp., Hoplocampa spp., Lasius spp., Monomorium pharaonis and Vespa spp. From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa. From the order of the Siphonaptera, for example, Xenopsylla cheopis and Ceratophyllus spp. From the order of the Arachnida, for example, Scorpio maurus and Latrodectus mactans.

The compounds of the general formula (I) according to the invention are distinguished by a very powerful insecticidal activity. They show excellent action, in particular when used against insects causing damage to plants, such as, for example, against moth caterpillars (for example Plutella maculipennis and Spodoptera spp.) and against beetle grubs (for example Phaedon cochleariae).

The active compounds of the formula (I) according to the invention are also suitable for controlling arthropods which occur in connection with the breeding and keeping of animals, for example of agricultural livestock, such as, for example, cattle, sheep, goats, horses, pigs, chickens etc., and other domestic animals such as, for example, dogs, cats, cage birds and aquarium fish. By controlling these arthropods cases of death and reductions in productivity (of meat, milk, wool, hides, eggs etc.) should be prevented or diminished, so that more economical and more simple keeping of animals is possible.

The application of the active compounds according to the invention occurs in the fashion customary in this sector, for example by dipping, spraying, pouring-on and spotting-on, washing, dusting, as well as by means of moulded articles containing the active compounds, such as neckbands, ear tags, tail tags, limb bands, halters, marking devices etc. As the active compounds are not absorbed in the animal body (thus behaving in an "inert" manner), they can also be employed in the form of suitable preparations (for example boli, granules) in the so-called feedthrough method (for example via the feed or drinking water), preventing or diminishing the development of insects in the animal excrements.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.000001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

In the present test, all the percentage data are based on per cent by weight, unless stated otherwise.

PREPARATION EXAMPLES

Example 1

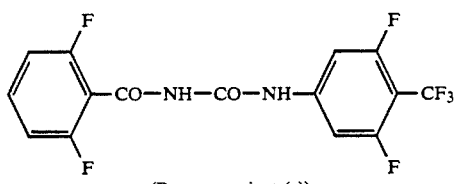

(Process variant (a))

A solution of 1.83 g (0.01 mol) of 2,6-difluorobenzoyl isocyanate in 10 ml of dry toluene is added dropwise at 40° C. to 1.97 g (0.01 mol) of 3,5-difluoro-4-trifluoromethyl-aniline in 60 ml of dry toluene. The batch is stirred at 80° C. for one hour. About ⅔ of the solvent are then distilled off in vacuo. About 10–15 ml of petroleum ether are added, and the precipitate is filtered off. It is rinsed with petroleum ether. The substance is dried at 50° C.–60° C. in vacuo.

3.6 g (95% of theory) of 1-(2,6-difluoro-benzoyl)3-(3,5-difluoro-4-trifluoromethyl-phenyl)-urea of melting point 231° C. are obtained.

The compounds of the formula (I) listed in the following Table 2 can be prepared in analogy to Example 1 and corresponding to the general description of process variants (a) and (b) according to the invention.

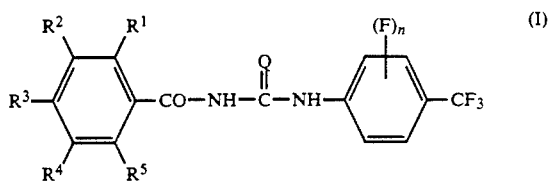

TABLE 2

Examples of the compounds of the formula (I)

| Example No. | Q | $R^1$ | $R^2$ | $R^3$ | $R^4$ | $R^5$ | (F)n-phenyl-CF₃ | Melting point (°C.) |
|---|---|---|---|---|---|---|---|---|
| 2 | S | Cl | H | H | H | Cl | 3,5-F,F-4-CF₃ | 259 (decomp.) |
| 3 | S | Cl | H | F | H | H | 3,5-F,F-4-CF₃ | 212 |
| 4 | S | Br | H | H | H | H | 3,5-F,F-4-CF₃ | 207 |
| 5 | S | Cl | H | H | H | H | 3,5-F,F-4-CF₃ | 198 |
| 6 | O | F | H | F | H | H | 3,5-F,F-4-CF₃ | 205 |
| 7 | O | CH₃ | H | H | H | H | 2,3,5,6-F,F,F,F-4-CF₃ | 198 |
| 8 | O | F | F | F | F | F | 2,3,5,6-F,F,F,F-4-CF₃ | 187 |
| 9 | O | Cl | H | Cl | F | H | 2,3,5,6-F,F,F,F-4-CF₃ | 192 |

TABLE 2-continued

Examples of the compounds of the formula (I)

| Example No. | Q | R¹ | R² | R³ | R⁴ | R⁵ | (F)ₙ–⟨ring⟩–CF₃ | Melting point (°C.) |
|---|---|---|---|---|---|---|---|---|
| 10 | O | Cl | H | H | F | H | 2,3,5,6-tetraF | 189 |
| 11 | O | F | H | F | H | H | 2,3,5,6-tetraF | 168 |
| 12 | S | Cl | H | H | H | H | 2,3,5,6-tetraF | 184 |
| 13 | S | Cl | H | H | H | F | 2,3,5,6-tetraF | 206 |
| 14 | S | F | H | H | H | F | 2,3,5,6-tetraF | 181 |
| 15 | O | Cl | H | H | H | H | 2,3,5,6-tetraF | 199 |
| 16 | O | Cl | H | F | H | H | 2,3,5,6-tetraF | 182 |
| 17 | O | Cl | H | H | H | F | 2,3,5,6-tetraF | 189 |
| 18 | O | F | H | H | H | F | 2,3,5,6-tetraF | 194 |
| 19 | S | F | H | H | H | F | 3,5-diF | 195 |
| 20 | O | Cl | H | F | H | H | 3,5-diF | 204 |
| 21 | O | Cl | H | H | H | H | 3,5-diF | 193 |
| 22 | O | F | H | F | H | H | 3,5-diF | 192 |
| 23 | O | Cl | H | H | H | F | 3,5-diF | 213 |
| 24 | O | F | H | H | H | F | 3,5-diF | 207 (decomp.) |
| 25 | S | Cl | H | F | H | H | 2,3,5-triF | 109 |
| 26 | O | Cl | H | H | H | H | 2,3,5-triF | 191 |
| 27 | O | Cl | H | F | H | H | 2,3,5-triF | 155 |
| 28 | O | Cl | H | H | H | F | 2,3,5-triF | 223 |
| 29 | O | F | H | H | H | F | 2,3,5-triF | 205 |
| 30 | O | Cl | H | H | H | H | 3-F | 211 |
| 31 | O | Cl | H | F | H | H | 3-F | 192 |

TABLE 2-continued

Examples of the compounds of the formula (I)

| Example No. | Q | R¹ | R² | R³ | R⁴ | R⁵ | (F)ₙ—⟨⟩—CF₃ | Melting point (°C.) |
|---|---|---|---|---|---|---|---|---|
| 32 | O | Cl | H | H | H | F | F, CF₃, F (2,4,6-F with CF₃) | 228 |
| 33 | S | F | H | H | H | F | F, CF₃, F, F | 158 |
| 34 | S | Cl | H | H | H | F | F, CF₃, F, F | 177 |
| 35 | S | Cl | H | H | H | H | F, CF₃, F, F | 142 |
| 36 | S | CH₃ | H | H | H | H | F, CF₃, F, F | 134 |
| 37 | S | F | H | H | H | H | F, CF₃, F, F | 134 |
| 38 | S | Cl | H | H | H | Cl | F, CF₃, F, F | 222 |
| 39 | S | Cl | H | H | F | H | F, CF₃, F, F | 112 |
| 40 | S | CF₃ | H | H | H | H | F, CF₃, F, F | 147 |
| 41 | S | Br | H | H | H | H | F, CF₃, F, F | 150 |
| 42 | S | H | H | H | H | H | F, CF₃, F, F | 158 |
| 43 | O | Br | H | H | H | H | F, CF₃, F, F | 191 |
| 44 | O | F | H | H | H | H | F, CF₃, F, F | 179 |
| 45 | O | CH₃ | H | H | H | H | F, CF₃, F, F | 208 |
| 46 | O | Cl | H | H | F | H | F, CF₃, F, F | 177 |
| 47 | O | H | H | H | H | H | F, CF₃, F, F | 245 |
| 48 | O | F | H | F | H | H | F, CF₃, F, F | 190 |
| 49 | O | Cl | H | Cl | F | H | F, CF₃, F, F | 177 |
| 50 | O | F | F | F | F | F | F, CF₃, F, F | 166 |
| 51 | O | NO₂ | H | H | H | H | F, CF₃, F, F | 189 |
| 52 | O | Cl | H | H | H | Cl | F, CF₃, F, F | 231 |
| 53 | O | Cl | H | Cl | H | H | F, CF₃, F, F | 173 |

TABLE 2-continued
Examples of the compounds of the formula (I)
| Example No. | Q | R¹ | R² | R³ | R⁴ | R⁵ | $(F)_n$ —⟨⟩—CF₃ | Melting point (°C.) |
|---|---|---|---|---|---|---|---|---|
| 54 | S | F | H | H | H | F |  | 201 |
| 55 | S | Cl | H | H | H | F |  | 212 |
| 56 | S | Cl | H | F | H | H |  | 123 |
| 57 | S | Cl | H | H | H | H |  | 159 |
| 58 | S | Cl | H | H | H | Cl |  | 228 |
| 59 | S | F | H | H | H | H |  | 123 |
| 60 | S | CH₃ | H | H | H | H |  | 143 |
| 61 | S | H | H | H | H | H |  | 141 |
| 62 | O | F | H | F | H | H |  | 199 |
| 63 | O | Cl | H | H | F | H |  | 191 |
| 64 | S | CF₃ | H | H | H | H |  | 145 |
| 65 | S | Cl | H | H | F | H |  | 153 |
| 66 | O | H | H | H | H | H | 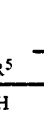 | 234 |
| 67 | O | Br | H | H | H | H |  | 215 |
| 68 | O | CH₃ | H | H | H | H |  | 230 |
| 69 | O | F | F | F | F | F |  | 176 |
| 70 | O | F | H | H | H | F |  | 195 |
| 71 | O | Cl | H | H | H | F |  | 198 |
| 72 | S | F | H | H | H | F | 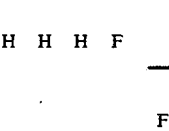 | 193 |
| 73 | S | Cl | H | F | H | H |  | 148 |
| 74 | S | Cl | H | H | H | F | 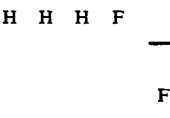 | 223 |

Starting substances of the formula (II)

Example (II-1)

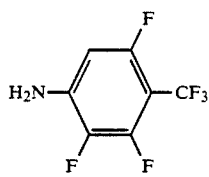

110 g of 2,3,4,6-tetrafluorobenzotrifluoride in 200 ml of tetrahydrofuran are initially introduced into a stainless steel autoclave of capacity 0.7 l, and 30 ml of liquid ammonia are injected. The batch is then heated at 100° C. for 3 hours (maximum pressure: 10 bar). After cooling, the pressure is released and the liquid phase is subjected to fractional distillation. First, at a boiling point of 47° C.–48° C./8 mbar, 42 g of 2,3,5-trifluoro-6-trifluoromethylaniline are obtained, and then, following an intermediate fraction and at a boiling point of 75° C.–78° C./ 8 mbar, 46 g of 2,3,5-trifluoro-4-trifluoromethylaniline.

Example (II-2)

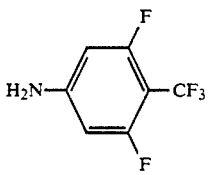

200 ml of tetrahydrofuran and 50 g of 2,4,6-trifluorobenzotrifluoride are initially introduced into a stainless steel autoclave, and 30 ml of liquid ammonia are injected. The batch is then heated to 120° C. for 6 hours and with stirring. The reaction mixture is cooled,- the pressure is released and the reaction mixture subjected to fractional distillation. At a boiling point of 57° C.-58° C./12 mbar, 15 g of 2-trifluoromethyl-3,5-difluoroaniline are obtained. After a small intermediate fraction 32 g of 3,5-difluoro-4-trifluoromethylaniline distil over at a boiling point of 103° C.–105° C./16 mbar (melting point: 66° C.).

Example (II-3)

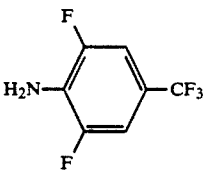

500 g of 3,4,5-trifluoro-benzotrifluoride are initially introduced into a stainless steel autoclave, 2000 ml of tetrahydrofuran are added and 150 g of liquid ammonia are injected. The autoclave is heated at 120° C.-130° C. for 5 hours and with stirring and then cooled and the pressure is released at 20° C. Beside the solvent and starting material, 272 g of 2,6-difluoro-4-trifluoromethylaniline (boiling point 58° C.-60° C./16 mbar) are obtained by distillation.

Example (II-4)

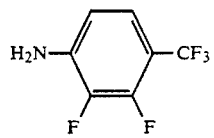

200 g of 2,3,4-trifluoro-benzotrifluoride in 500 ml of tetrahydrofuran are initially introduced into an autoclave, and 60 ml of liquid ammonia are injected. The batch is stirred at 130° C. (maximum pressure 18 bar) for 6 hours and then cooled and the pressure is released. At a boiling point of 92° -93° C./26 mbar, 92 g of 2,3-difluoro-4-trifluoromethylaniline are obtained by distillation.

Example A

Phaedon larvae test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), as long as the leaves are still moist.

After the specified periods of time, the destruction in % is determined. 100% means that all the beetle larvae have been killed; 0% means that none of the beetle larvae have been killed.

In this test, for example, the compounds of Preparation Examples (1), (30) and (32) showed a destruction of 100% after 10 days, at an illustrative concentration of 0.0001 %.

Example B

Plutella test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the diamond-back moth (Plutella maculipennis), as long as the leaves are still moist.

After the specified periods of time, the destruction in % is determined. 100% means that all the caterpillars have been killed; 0% means that none of the caterpillars has been killed.

In this test, for example, the compounds of Preparation Examples (1), (26), (30) and (31) showed a destruction of 100 % after 7 days, at an illustrative concentration of 0.00001%.

Example C

Spodoptera test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the owlet moth (Spodoptera frugiperda), as long as the leaves are still moist.

After the desired time, the destruction in % is determined. 100% means that all the caterpillars have been killed; 0% means that none of the caterpillars has been killed.

In this test, for example the compounds of Preparation Examples (1), (25), (26), (27), (28), (29), (30), (31) and (32) showed a destruction of 100 % after 7 days, at an illustrative concentration of 0.0001%.

Example D

Test with Lucilia cuprina resistant larvae

Solvent: 35 parts by weight of ethylene glycol monomethyl ether, 35 parts by weight of nonylphenol polyglycol ether.

To produce a suitable preparation of active compound, three parts by weight of active compound are mixed with seven parts by weight of the abovementioned mixture and the concentrate thus obtained is diluted with water to the particular desired concentration.

About 20 Lucilia cuprina resistant larvae are introduced into a test tube which contains approximately 1 cm³ of horse muscle and 0.5 ml of the preparation of active compound. After 24 hours, the degree of destruction is determined.

In this test, for example the compounds of Preparation Examples (25), (26), (27) and (29) showed a degree of destruction of 100% at an illustrative concentration of 100 ppm.

It will be appreciated that the instant specification and claims are set forth by way of illustration and not limitation, and that various modifications and changes may be made without departing from the spirit and scope of the present invention.

What is claimed is:

1. A substituted benzoyl(thio)urea of the formula

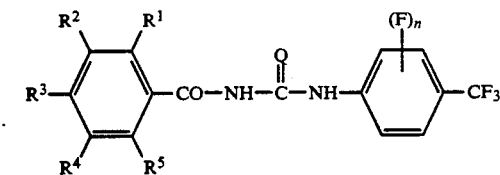

(I)

in which

Q stands for oxygen or sulphur,
$R^1$ stands for hydrogen, halogen, nitro, methyl or trifluoromethyl,
$R^2$ stands for hydrogen, fluorine or chlorine,
$R^3$ stands for hydrogen, fluorine or chlorine,
$R^4$ stands for hydrogen or fluorine,
$R^5$ stands for hydrogen or halogen and
n stands for the numbers 2, 3 or 4,
excluding compounds in which simultaneously
$R^1$ and $R^5$ stand for fluorine,
$R^2$ and $R^4$ stand for hydrogen,
$R^3$ stands for hydrogen or fluorine,
Q stands for oxygen, and
$(F)_n$ stands for 2,5-di-fluoro.

2. A compound according to claim 1, in which
Q stands for oxygen or sulphur,
$R^1$ stands for hydrogen, fluorine, chlorine, nitro, methyl or trifluoromethyl,
$R^2$ stands for hydrogen, fluorine or chlorine,
$R^3$ stands for hydrogen, fluorine or chlorine,
$R^4$ stands for hydrogen or fluorine,
$R^5$ stands for hydrogen, fluorine and chlorine and
n stands for the numbers 2, 3 or 4, 3. A compound according to claim 1, in which
Q stands for oxygen or sulphur,
$R^1$ stands for fluorine or chlorine,
$R^2$ stands for hydrogen,
$R^3$ stands for hydrogen and fluorine,
$R^4$ stands for hydrogen and fluroine,
$R^5$ stands for hydrogen and fluorine and
n stands for the numbers 2,3 or 4.

4. A compound according to claim 1, in which
Q stands for oxygen,
$R^1$ stands for fluorine or chlorine,
$R^2$ stands for hydrogen,
$R^3$ stands for hydrogen and fluorine,
$R^4$ stands for hydrogen,
$R^5$ stands for hydrogen and fluorine and
n stands for the numbers 2,3 or 4.

5. A compound according to claim 4, in which $(F)_n$ are in the 3,5- or 3,5,6-positions of the phenyl ring.

6. A compound according to claim 1, wherein such compound is 1-(2,6-difluoro-benzoyl)-3-(3,5-difluoro-4-trifluoromethylphenyl)-urea of the formula

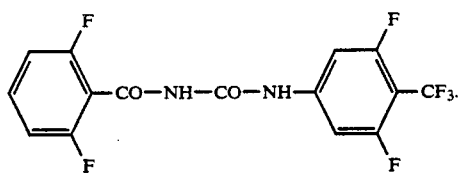

7. A compound according to claim 1, wherein such compound is 1-(2-chloro-4-fluoro-benzoyl)-3-(2,3,5-trifluoro-4-trifluoromethyl-phenyl)-urea of the formula

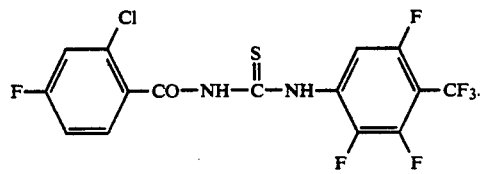

8. A compound according to claim 1, wherein such compound is 1-(2-chloro-benzoyl)-3-(3,5-difluoro-4-trifluoromethyl-phenyl)-urea of the formula

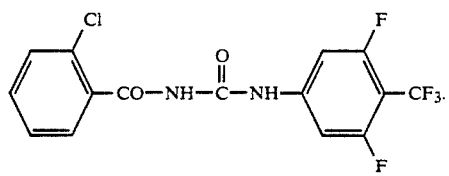

9. A compound according to claim 1, wherein such compound is 1-(2-chloro-4-fluoro-benzoyl)-3-(3,5-difluoro-4-trifluoromethyl-phenyl)-urea of the formula

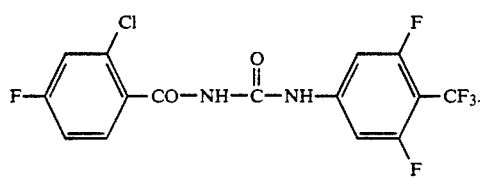

10. A compound according to claim 1, wherein such compound is 1-(2-chloro-6-fluoro-benzoyl)-3-(3,5-difluoro-4-trifluoromethyl-phenyl)-urea of the formula

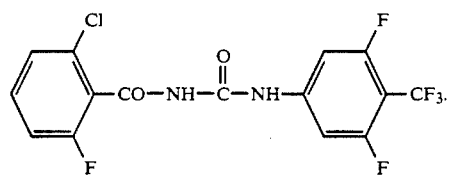

11. A compound according to claim 1, in which

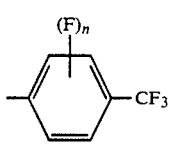

stands for

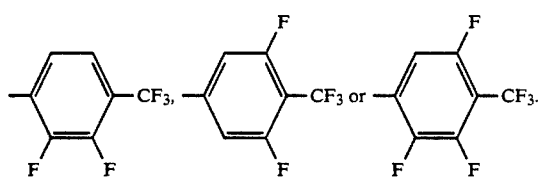

12. A compound according to claim 1, in which

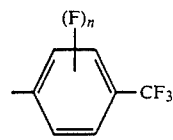

stands for

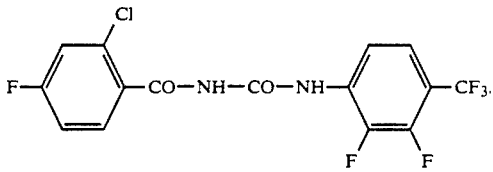

13. A compound according to claim 1, wherein such compound is 1-(2-chloro-4-fluoro-benzoyl)-3-(2,3-difluoro-4-trifluoromethyl-phenyl)-urea of the formula

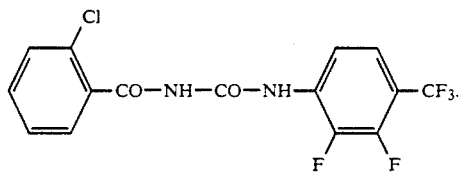

14. A compound according to claim 1, wherein such compound is 1-(2-chloro-4-fluoro-benzoyl-3-(2,3-difluoro-4-trifluoromethyl-phenyl)-urea of the formula

[structure]

15. An insecticidal composition comprising an insecticidally effective amount of a compound according to claim 1 and diluent.

16. A method of combating insects which comprises applying to such insects or to an insect habitat an insecticidally effective amount of a compound according to claim 1.

17. The method according to claim 16, wherein such compound is 1-(2,6-difluoro-benzoyl)-3-(3,5-difluoro-4-trifluoromethyl-phenyl)-urea,
1-(2-chloro-4-fluoro-benzoyl)-3-(2,3,5-trifluoro-4-trifluoromethyl-phenyl)-urea,
1-(2-chloro-benzoyl)-3-(3,5-difluoro-4-trifluoromethyl-phenyl)-urea,
1-(2-chloro-4-fluoro-benzoyl)-3-(3,5-difluoro-4-trifluoromethyl-phyenyl)-urea,
1-(2-chloro-4-benzoyl)-3-(2,3-difluoro-4-trifluoromethyl-phenyl)-urea, or
1-(2-chloro-4-fluoro-benzoyl)-3-(2,3-difluoro-4-trifluoromethyl-phenyl)-urea, or
1-(2-chloro-benzoyl)-3-(2,3-difluoro-4-trifluoromethyl-phenyl)-urea.

* * * * *

UNITED STATES PATENT AND TRADEMARK OFFICE
CERTIFICATE OF CORRECTION

PATENT NO. : 5,096,928

DATED : March 17, 1992

INVENTOR(S) : Sirrenberg et al.

It is certified that error appears in the above-identified patent and that said Letters Patent is hereby corrected as shown below:

Col. 24, line 58  Delete " 4-benzoyl)-3-(2,3-difluoro " and substitute -- 6-fluoro-benzoyl)-3-(3,5-difluoro --

Signed and Sealed this

Twenty-first Day of December, 1993

Attest:

BRUCE LEHMAN

Attesting Officer    Commissioner of Patents and Trademarks